United States Patent
Marchionni et al.

(10) Patent No.: US 7,132,051 B2
(45) Date of Patent: Nov. 7, 2006

(54) LIQUID-LIQUID EXTRACTION OF POLAR ORGANIC SUBSTANCES FROM THEIR AQUEOUS SOLUTIONS WITH FLUORINATED EXTRACTING LIQUIDS

(75) Inventors: Giuseppe Marchionni, Milan (IT); Ugo De Patto, Milan (IT); Marco Avataneo, Milan (IT)

(73) Assignee: Solvay Solexis, S.p.A., Milan (IT)

(*) Notice: Subject to any disclaimer, the term of this patent is extended or adjusted under 35 U.S.C. 154(b) by 218 days.

(21) Appl. No.: 10/384,665

(22) Filed: Mar. 11, 2003

(65) Prior Publication Data
US 2003/0173310 A1    Sep. 18, 2003

(30) Foreign Application Priority Data
Mar. 12, 2002   (IT)   ........................... MI2002A0513

(51) Int. Cl.
*B01D 11/00* (2006.01)
(52) U.S. Cl. .................... 210/634; 203/39; 203/71; 210/774
(58) Field of Classification Search .......... 210/634, 210/770, 774, 806; 202/168–170, 175; 203/14–19, 203/39, 45, 71; 570/178; 568/842
See application file for complete search history.

(56) References Cited

U.S. PATENT DOCUMENTS

| | | | |
|---|---|---|---|
| 3,846,488 A | 11/1974 | Otsuki et al. | |
| 4,582,570 A | 4/1986 | Mix | |
| 5,000,830 A | 3/1991 | Marchionni et al. | |
| 5,144,092 A | 9/1992 | Marraccini et al. | |
| 5,149,842 A | 9/1992 | Sianesi et al. | |
| 5,220,082 A | 6/1993 | Krespan | |
| 5,225,048 A * | 7/1993 | Yuan | 203/1 |
| 5,713,211 A | 2/1998 | Sherwood | |
| 6,046,368 A * | 4/2000 | Lamanna et al. | 568/683 |
| 6,121,497 A | 9/2000 | Murphy | |
| 6,235,701 B1 * | 5/2001 | Senger Elsbernd | 510/412 |
| 6,572,831 B1 * | 6/2003 | Nicola | 422/256 |

FOREIGN PATENT DOCUMENTS

| | | |
|---|---|---|
| EP | 0 695 775 B1 | 12/1998 |
| EP | 0 982 281 A1 | 3/2000 |
| WO | WO 00/44697 | 8/2000 |

OTHER PUBLICATIONS

Handbook of Separation Techniques for Chemical Engineers, Schweitzer Editor-in-chief, published 1979, Section 1.6 Solvent Recovery edited by Drew, pp. 1-201 through 1-219.*

* cited by examiner

*Primary Examiner*—Joseph Drodge
(74) *Attorney, Agent, or Firm*—Arent Fox PLLC

(57) ABSTRACT

A liquid-liquid extraction process of ketones, alcohols, aldehydes, alkyl esters of carboxylic acids, carboxylic acids, ethers, amines and heterocyclic compounds, from their aqueous solutions, comprising the addition under stirring to said aqueous solutions of a fluorinated extracting liquid selected from
A) hydrofluoropolyethers,
B) hydrofluorocarbons,
C) hydrofluoroethers,
or mixtures thereof, with formation of an aqueous phase and of an organic phase; the separation of the organic phase from the aqueous phase; the fractional distillation of the organic phase to separate the polar organic substance from the extractant.

13 Claims, No Drawings

LIQUID-LIQUID EXTRACTION OF POLAR ORGANIC SUBSTANCES FROM THEIR AQUEOUS SOLUTIONS WITH FLUORINATED EXTRACTING LIQUIDS

The present invention relates to a process for recovering polar organic substances from their aqueous solutions by liquid-liquid extraction with a solvent consisting of a fluorinated fluid.

More specifically the present ivnention relates to a process to separate polar organic substances such for example ketones, alcohols, aldehydes, alkyl esters of carboxylic acids, carboxylic acids, ethers, amines and heterocyclic substances, from their aqueous solutions by contact of said solutions with fluorinated fluids selected from hydrofluoropolyethers, hydrofluoroethers, hydrofluorocarbons and/or their mixtures with perfluoropolyethers and/or perfluorocarbons.

The separation of polar organic substances from their aqueous solutions is generally carried out by fractional distillation. However, when the polar organic substances have boiling points close to that of the water, in the order of ±10° C., more specifically ±5° C., or form therewith azeotropes, or like-azeotropic or near-azeotropic mixtures, their separation by fractional distillation results difficult and expensive or impossible.

For the aforesaid separations in the prior art the use of solvents to selectively extract the organic substance from the water, using liquid-liquid extraction columns or extractive distillation columns has been made.

In U.S. Pat. No. 6,121,497 the methylethylketone (MEK) is separated from an aqueous mixture containing MEK and ethanol, by liquid-liquid extraction with a solvent selected between isopentane and xylene, by using a column having 20 plates and subsequently by distilling the MEK/solvent mixture in a column having 36 plates to separate the MEK from the solvent.

In patent application WO 00/44,697 ethanol is separated from its aqueous solutions by using an extractive distillation solvent selected from amines and chlorinated hydrocarbons.

Said known methods, however, are complicated and expensive and require toxic and/or flammable and/or harmful solvents for the environment.

It has been unexpectedly and surprisingly found a process which allows to separate said polar organic substances from their aqueous solutions, by liquid-liquid extraction with an extractant selected from specific fluorinated liquids which do not show the drawbacks of those of the prior art.

An object of the present invention is therefore a liquid-liquid extraction process of polar organic substances, completely or partially soluble in water, from their aqueous solutions, comprising:

1) addition to said aqueous solutions of a fluorinated extracting liquid selected from
   A) hydrofluoropolyethers,
   B) hydrofluorocarbons,
   C) hydrofluoroethers,
   or mixtures thereof, wherein A), B) and C) have a molecular weight in the range 82–12,000, preferably 180–5,000, and when A) is a polymer the molecular weight is a number average weight,
   with formation of an aqueous phase and of an organic phase;
2) separation of the organic phase, formed by the fluorinated extractant containing the polar organic substance, from the aqueous phase;
3) fractional distillation of the organic phase to separate the polar organic substance from the extractant.

The process is particularly advantageous when the polar organic substances form with water an azeotropic mixture or near azeotropic mixtures, or have a boiling point with respect to water, in the order of ±10° C., more specifically ±5° C.

According to the present invention with near azeotropic mixtures, the mixtures of polar organic substances with water are meant, having the vapour composition, in balance with the liquid phase, substantially equal to the liquid composition.

Classes of polar organic substances which can be separated from the water by the above process are ketones, alcohols, aldehydes, alkyl esters of carboxylic acids, carboxylic acids, ethers, amines and heterocyclic compounds. Specific examples of said substances are, for example, methylethylketone, triethylamine, and ethyl acetate.

Generally the substances of the class A), B) and C) are extractants which are liquid under the ambient conditions, 25° C. and 1 atm. It is also possible to use the extractants of said classes which are not liquid at the ambient conditions provided that one works under pressure or at temperatures lower than the boiling temperature so that the process is carried out in liquid phase.

The class A) hydrofluoropolyethers comprise one or more oxy(per)fluoroalkylene units selected from —$(CF_2(CF_2)_cO)$— wherein c=1, 2, 3;

—$(CF_2O)$—;

—$(CF_2CF(CF_3)O)$—;

—$(CF(CF_3)O)$—;

—$(CF_2CF(OX)O)$—;

—$(CF(OX)O)$— wherein X=—$(Y)_nCF_3$ wherein Y=—$CF_2$—, —$CF_2O$—, —$CF_2CF_2O$—, —$CF_2CF(CF_3)O$—, and n=0, 1, 2, 3, 4; said units being statistically distributed in the polymer chain.

The preferred compounds of class A) are hydroperfluoropolyethers having formula (I):

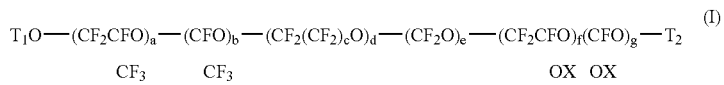

wherein X has the above meaning; the coefficients a, b, d, e, f, g are 0 or integers, c is 1, 2 or 3, selected so that their sum results such that the number average molecular weight is in the range 82–12,000, preferably 180–5,000; $T_1$, $T_2$, equal to or different from each other, are selected from —$CF_2H$, —$CF(CF_3)H$, —$CF_2CF_2H$, —$CH_3$, —$C_2H_5$.

The compounds of formula (I) show a low environmental impact. In particular they show an ODP=0 and a low potential greenhouse effect (GWP).

Examples of formula (I) compounds having —$CH_3$ end groups, are the following:

| | Molecular Weight (MWn) |
|---|---|
| $CH_3OCF_2CF_2OCH_3$ | 162 |
| $CH_3OCF_2CF_2OCF_2CF_2OCH_3$ | 278 |
| $CH_3OCF_2CF_2OCF_2OCF_2CF_2OCH_3$ | 344 |
| $CH_3O(CF_2CF_2O)_3CH_3$ | 394 |
| $CH_3OCF_2CF_2O(CF_2O)_2CF_2CF_2OCH_3$ | 410 |
| $CH_3OCF_2CF_2OCF_2OCF_2CF_2OCF_2CF_2OCH_3$ | 460 |
| $CH_3O(CF_2CF_2O)_4CH_3$ | 510 |
| $CH_3OCF_2CF_2OCF_2O(CF_2CF_2O)_2CF_2CF_2OCH_3$ | 576 |
| $CH_3O(CF_2CF_2O)_5CH_3$ | 626 |

Examples of formula (I) compounds having —$C_2H_5$ end groups, are the following:

| | MWn |
|---|---|
| $CH_3CH_2OCF_2CF_2OCH_2CH_3$ | 190 |
| $CH_3CH_2OCF_2CF_2OCF_2CF_2OCH_2CH_3$ | 306 |
| $CH_3CH_2OCF_2CF_2OCF_2OCF_2CF_2OCH_2CH_3$ | 372 |
| $CH_3CH_2O(CF_2CF_2O)_3CH_2CH_3$ | 422 |
| $CH_3CH_2OCF_2CF_2O(CF_2O)_2CF_2CF_2OCH_2CH_3$ | 438 |
| $CH_3CH_2OCF_2CF_2OCF_2OCF_2CF_2OCF_2CF_2OCH_2CH_3$ | 488 |
| $CH_3CH_2O(CF_2CF_2O)_4CH_2CH_3$ | 538 |
| $CH_3CH_2OCF_2CF_2OCF_2O(CF_2CF_2O)_2CF_2CF_2OCH_2CH_3$ | 604 |
| $CH_3CH_2O(CF_2CF_2O)_5CH_2CH_3$ | 654 |

Examples of formula (I) compounds having —$CH_3$ and —$CF_2H$ end groups, are the following:

| | MWn |
|---|---|
| $CH_3OCF_2H$ | 82 |
| $CH_3OCF_2CF_2OCF_2H$ | 198 |
| $CH_3OCF_2CF_2OCF_2OCF_2H$ | 264 |
| $CH_3O(CF_2CF_2O)_2CF_2H$ | 314 |
| $CH_3OCF_2CF_2O(CF_2O)_2CF_2H$ | 330 |
| $CH_3OCF_2CF_2OCF_2OCF_2CF_2OCF_2H$ | 380 |
| $CH_3O(CF_2CF_2O)_3CF_2H$ | 430 |
| $CH_3OCF_2CF_2OCF_2O(CF_2CF_2O)_2CF_2H$ | 496 |
| $CH_3O(CF_2CF_2O)_4CF_2H$ | 546 |

Examples of formula (I) compounds having —$C_2H_5$ and —$CF_2H$ end groups, are the following:

| | MWn |
|---|---|
| $CH_3CH_2OCF_2H$ | 96 |
| $CH_3CH_2OCF_2CF_2OCF_2H$ | 212 |
| $CH_3CH_2OCF_2CF_2OCF_2OCF_2H$ | 278 |
| $CH_3CH_2O(CF_2CF_2O)_2CF_2H$ | 328 |
| $CH_3CH_2OCF_2CF_2O(CF_2O)_2CF_2H$ | 344 |
| $CH_3CH_2OCF_2CF_2OCF_2OCF_2CF_2OCF_2H$ | 394 |
| $CH_3CH_2O(CF_2CF_2O)_3CF_2H$ | 444 |
| $CH_3CH_2OCF_2CF_2OCF_2O(CF_2CF_2O)_2CF_2H$ | 510 |
| $CH_3CH_2O(CF_2CF_2O)_4CF_2H$ | 560 |

Particularly preferred compounds of formula (I) are those of formula (II):

$$T_1O-(CF_2CF_2O)_d-(CF_2O)_e-T_2 \quad (II)$$

wherein $T_1$, $T_2$=—$CF_2H$ and d, e are as defined in formula (I).

Examples of formula (II) compounds are the following:

| | MWn | b.p. (° C.) |
|---|---|---|
| $HCF_2OCF_2OCF_2H$ | 184 | 35 |
| $HCF_2OCF_2CF_2OCF_2H$ | 234 | 58–59 |
| $HCF_2OCF_2OCF_2OCF_2H$ | 250 | 68 |
| $HCF_2OCF_2OCF_2CF_2OCF_2H$ | 300 | 85–86 |
| $HCF_2OCF_2CF_2OCF_2CF_2OCF_2H$ | 350 | 98.5 |
| $HCF_2(OCF_2)_2OCF_2CF_2OCF_2H$ | 366 | 109 |
| $HCF_2OCF_2(OCF_2CF_2)_2OCF_2H$ | 416 | 123 |
| $HCF_2(OCF_2CF_2)_3OCF_2H$ | 466 | 133 |
| $HCF_2(OCF_2)_2(OCF_2CF_2)_2OCF_2H$ | 482 | 142 |
| $HCF_2OCF_2(OCF_2CF_2)_3OCF_2H$ | 532 | 151 |
| $HCF_2(OCF_2CF_2)_4OCF_2H$ | 582 | 160 |
| $HCF_2(OCF_2)_2(OCF_2CF_2)_3OCF_2H$ | 593 | 169 |
| $HCF_2OCF_2(OCF_2CF_2)_4OCF_2H$ | 648 | 175 |
| $HCF_2(OCF_2CF_2)_5OCF_2H$ | 698 | 183 |
| $HCF_2(OCF_2)_2(OCF_2CF_2)_4OCF_2H$ | 714 | 190 |
| $HCF_2OCF_2(OCF_2CF_2)_5OCF_2H$ | 764 | 196 |

Mixtures of said hydrofluoropolyethers or mixtures of hydrofluoropolyethers with perfluoropolyethers having the same formula (I) but with $T_1=T_2$ selected between —$CF_2X_1$ ($X_1$=—F, —$CF_3$), —$C_3F_7$ can also be used.

The perfluoropolyether amount in said mixture is in the range 0–50% by weight, preferably 0–20% by weight.

The class B) compounds are preferably selected from those liquid under the ambient conditions, such as for example $CF_3CF_2$—CFH—CFH—$CF_3$, cyclo-$C_5F_8H_3$, cyclo-$C_5F_9H_2$.

Mixtures of class A) hydrofluoropolyethers with class B) hydrofluorocarbons can also be used.

The class C) compounds are preferably hydrofluoroethers of general formula (III):

$$R_1-O-R_2 \quad (III)$$

wherein $R_1$, $R_2$, equal to or different from each other, are alkyls comprising together at least 3 carbon atoms, wherein at least one of the $R_1$, $R_2$ contains at least one fluorine atom and wherein the total number of hydrogen atoms is equal at most to the number of the fluorine atoms. Preferably to increase the non flammability the number of fluorine atoms is higher than the number of hydrogen atoms. Optionally $R_1$ and/or $R_2$ can contain one or more ether oxygen atoms.

Specific examples are $C_3F_7$—O—$CH_3$, $C_3F_7$—O—$C_2H_5$, $C_4F_9$—$OCH_3$, $C_4F_9$—O—$C_2H_5$, $C_7F_{15}$—O—$C_2H_5$, $C_4F_9$—O—$CF_2H$, $C_4F_9$—O—$CF_2CF_2H$.

The formula (I) compounds having both the end groups —$CH_3$, or —$C_2H_5$, or having one end group selected between —$CH_3$, —$C_2H_5$, and the other —$CF_2H$, can be prepared with the following method. The perfluoropolyethers, corresponding to those of formula (I), having —COF end groups are reacted with an alkaline metal fluoride (M) to give the corresponding alcoholates having —$CF_2OM$ end groups, which are reacted with methyl- or ethyl-sulphite, at temperatures between 110° C. and 200° C. The so obtained reaction mixture is salified with a base, then it is distilled under steam flow obtaining an aqueous residue and a distillate from which an organic phase is separated formed by the formula (I) compound wherein $T_1$ and $T_2$ are methyl or ethyl. The residue of the aforesaid distillation is acidified with an HCl solution, distilled under vacuum, in a range from 70° C. to 170° C., separating from the distillate an organic phase formed by a formula (I) product wherein $T_1$ is —$CH_3$ or —$C_2H_5$ and $T_2$ is —$CF_2COOH$, which is salified with KOH or NaOH, subsequently decarboxylated by known methods obtaining the compound of formula (I) wherein $T_1$ is —$CH_3$ or —$C_2H_5$ and $T_2$ is —$CF_2H$.

The hydrofluoropolyethers of formula (II) are known for example from EP 695,775.

The perfluoropolyethers are known products, for example from U.S. Pat. No. 5,149,842, U.S. Pat. No. 5,000,830, U.S. Pat. No. 5,144,092.

The class B) compounds are known, for example, from U.S. Pat. No. 5,220,082, EP 982,281.

The class C) hydrofluoroethers are known, for example, from U.S. Pat. No. 5,713,211.

All the compounds of the classes A), B) and C) have an impact on the ozone equal to zero (ODP=0), are not toxic, are not flammable, show a high thermal and chemical stability and a low potential greenhouse effect (GWP).

The treatment of step 1) of the invention process can be carried out by mixing the fluorinated extractant with the aqueous solution in a prefe-rably stirred system, at temperatures in the range 0° C.–50° C., preferably 15° C.–30° C., and at atmospheric pressure or higher so that the fluorinated solvent is in liquid phase. Step 1) can be carried out continuously by using, for example, a column in which the extractant fed to the aqueous solution.

The aqueous phase separated in 2) can be subjected to successive extractions with recycle of the extractant.

The recovered extractant in step 3) can be reused for subsequent extractions.

The aqueous solutions to be subjected to the extraction process can contain from 0.1 to 99% by weight of completely dissolved polar organic substance.

The ratio by weight between the aqueous solution containing the polar organic compound and the fluorinated extractant can be in the range 0.005–50, preferably 0.01–10.

If the amount of the extracted polar substance is low, it is possible to increase the extraction yield by increasing the fluorinated extractant amount or, as said above, by subjecting the aqueous phase, after the first extraction, to subsequent extractions. For example to extract isopropanol if one operates at 1:1 ratios and with a fluorinated extractant having molecular weight 655, in a single step, an extraction equal to 4% is obtained. To increase the extracted isopropanol amount, one can operate with a 1:78 ratio with a fluorinated solvent having molecular weight 1583, so obtaining an extraction yield of about 10 times higher.

The process appears particularly advantageous for the separation of polar organic substances forming azeotropes with the water or which have boiling points very close to that of the water, or which form near azeotropic mixtures with the water.

The present process results furthermore advantageous since it makes it possible the use of fluorinated extractants having boiling points very different from the boiling point of the polar organic substance, which allows the use, in the separation step 3), of a simple fractional distillation, with a limited plate number.

With the present process it is possible to obtain extraction yields higher than 90% in a single step, as in the case of aqueous mixtures containing ketones, amines and esters, in particular MEK, and purities of the extracted polar organic substance higher than 98%.

A further advantage of the present invention process is due to the chemical inertia of the fluorinated extractant which allows also the separation of reactive or unstable polar organic substances.

The invention process can also be used in the purification of industrial waters from polar organic substances or from organic solvents present in a low or high amount.

Some Examples follow for illustrative and not limitative purposes of the present invention.

EXAMPLES

Example 1

An aqueous solution MEK-water containing 86.7% of methylethylketone (MEK) $CH_3COCH_2CH_3$ has been used which being close to the azeotrope MEK-water was not possible to separate by fractional distillation.

100 g of aqueous solution containing 86.7 g of methylethylketone (MEK) are introduced into a 250 ml flask equipped with stirrer. 122 g of hydroperfluoropolyether having structure of formula (II) are introduced into the same, wherein $T_1=T_2=$—$CF_2H$ and is formed for 12% by weight by the oligomer having d=4, e=0, for 18% by the oligomer having d=3 and e=2, for 28% by the oligomer having d=4 and e=1, for 30% by the oligomer having d=5 and e=0, for 8% by the oligomer having d=4 and e=2 and for 4% by the oligomer having d=5 and e=1, with number average molecular weight of 655 having a boiling temperature of 178° C., visco-sity at 25° C. equal to 1,50 cSt. The mixture is put under stirring for 30 minutes and then discharged in a 250 ml separatory funnel. The lower organic phase is discharged and analyzed. 210 g of solution containing 83.2 g of MEK corresponding to 96.0% of the initially present MEK are recovered.

The 210 g of organic phase have been subjected to fractional distillation at a temperature of 79° C. obtaining 83 g of distillate containing 98.3% of MEK and 1.7% of water with a MEK yield of 94.1% and a purity of 98.3%.

Example 2

33 g of aqueous solution containing 1.4 g of methylethylketone (MEK) $CH_3COCH_2CH_3$ are introduced into a 100 ml flask equipped with stirrer. 64.7 g of hydrofluoropolyether used in Example 1 are fed to the same.

After separation of the organic phase 66 g of solution containing 1.9% by weight of methylethylketone corresponding to 89.6% of the fed methylethylketone and 0.03% of water are obtained.

Example 3

40 g of aqueous solution containing 1.7 g of methylethylketone (MEK) are introduced into a 100 ml flask equipped with stirrer. 39.8 g of hydrofluoropolyether used in Example 1 are fed to the same.

After separation 41 g of solution containing 2.9% by weight of methylethylketone corresponding to 69.9% of the fed methylethylketone and 0.04% of water are obtained.

Example 4

77.8 g of aqueous solution containing 3.3 g of methylethylketone (MEK) are introduced into a 250 ml flask equipped with stirrer. 38.4 g of hydrofluoropolyether used in Example 1 are fed to the same.

After separation 40 g of solution containing 3.9% by weight of methylethylketone corresponding to 47.3% of the fed methylethylketone are obtained.

Example 5

41.5 g of aqueous solution containing 10.7 g of methylethylketone (MEK) are introduced into a 100 ml flask equipped with stirrer. 21 g of hydrofluoropolyether used in Example 1 are fed to the same.

After separation 27.3 g of solution containing 22.8% by weight of methylethylketone corresponding to 58.2% of the fed methylethylketone and 0.4% of water are obtained.

Example 6

50 g of aqueous solution containing 43.4 g of methylethylketone (MEK) are introduced into a 250 ml flask equipped with stirrer. 60 g of a commercial sample of hydrofluoroether HFE 7500 by 3M are fed to the same, having structure

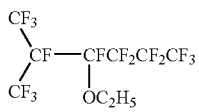

with molecular weight 414 having a boiling point of 123.5° C., viscosity at 25° C. equal to 1,33 cSt. The mixture is put under stirring for 35 minutes and then discharged into a 250 ml separatory funnel. The lower organic phase is discharged and analyzed.

104 g of solution containing 40.8 g of MEK corresponding to 94.0% of the initially present MEK are recovered.

Example 7

76.3 g of aqueous solution containing 68.6 g of ethanol $CH_3CH_2OH$ are introduced into a 250 ml flask equipped with stirrer. 77.4 g of hydrofluoropolyether used in Example 1 are fed to the same. The mixture is put under stirring for 30 minutes and then discharged into a 250 ml separatory funnel. The lower organic phase is discharged and analyzed.

67.7 g of solution containing 3.2 g of ethanol corresponding to 4.7% of the initially present ethanol are recovered.

Example 8

189 g of aqueous solution containing 141.9 g of isopropanol $(CH_3)_2CHOH$ are introduced into a 500 ml flask equipped with stirrer. 184 g of hydrofluoropolyether used in Example 1 are fed to the same. The mixture is put under stirring for 45 minutes and then discharged into a 500 ml separatory funnel. The lower organic phase is discharged and analyzed.

180 g of solution containing 6.1 g of isopropanol corresponding to 4.3% of the initially present isopropanol are recovered.

Example 9

1.7 g of aqueous solution containing 0.5 g of isopropanol are treated with 133.3 g of an hydrofluoropolyether having structure of formula (II) wherein $T_1=T_2=\!\!-\!\!CF_2H$ with d/e=1.1 having number average molecular weight of 1583, viscosity at 20° C. equal to 6.34 cSt in a 100 ml flask equipped with stirrer.

After separation 133.6 g of a solution containing 0.17% by weight of isopropanol corresponding to 45% of the fed isopropanol and 0.03% of water are recovered.

Example 10

20 g of aqueous solution containing 1.3 g of triethylamine $(CH_3CH_2)_3N$ are introduced into a 100 ml flask equipped with stirrer. 31.2 g of hydrofluoropolyether used in Example 1 are fed to the same. The mixture is put under stirring for 30 minutes and then discharged into a 100 ml separatory funnel. The lower organic phase is discharged and analyzed.

32.4 g of solution containing 1.2 g of triethylamine corresponding to 92.3% of the initially present triethylamine are recovered.

Example 11

31.5 g of aqueous solution containing 19.6 g of formic acid HCOOH are introduced into a 200 ml flask equipped with stirrer. 82.8 g of hydrofluoropolyether having structure of formula (II) are fed to the same, wherein $T_1=T_2=\!\!-\!\!CF_2H$ and it is formed for 11.8% by weight by the oligomer having d=0 and e=1, for 88.1% by the oligomer having d=1 and e=0 and for 0.1% by the oligomer having d=1 and e=1 with number average molecular weight of 228 having a boiling point of 51.5° C., viscosity at 25° C. equal to 0.37 cSt. The mixture is put under stirring for 30 minutes and then discharged into a 200 ml separatory funnel.

After separation 83.8 g of a solution containing 1.2% by weight of formic acid (corresponding to 5.1% of the fed formic acid) and 0.3% of water are obtained.

Example 12

35 g of aqueous solution containing 17.1 g of diglyme $(CH_3OCH_2CH_2)_2O$ are introduced into a 100 ml flask equipped with stirrer. 35.8 g of hydrofluoropolyether used in Example 1 are fed to the same. The mixture is put under stirring for 30 minutes and then discharged into a 100 ml separatory funnel.

After separation 41.2 g of a solution containing 12.9% by weight of diglyme corresponding to 31.1% of the fed diglyme and to 0.2% of water are obtained.

Example 13

35.1 g of aqueous solution containing 14.8 g of pyridine $C_5H_5N$ are introduced into a 100 ml flask equipped with stirrer. 49.6 g of hydrofluoropolyether used in Example 1 are fed to the same. The mixture is put under stirring for 30 minutes and then discharged into a 100 ml separatory funnel. The lower organic phase is discharged and analyzed.

51.7 g of solution containing 2.1 g of pyridine corresponding to 14.2% of the initially present pyridine are recovered.

Example 14

27.8 g of aqueous solution containing 2.0 g of ethyl acetate $CH_3COOCH_2CH_3$ are introduced into a 100 ml flask equipped with stirrer. 29.0 g of hydrofluoropolyether used in Example 1 are fed to the same. The mixture is put under stirring for 30 minutes and then discharged into a 100 ml separatory funnel. The lower organic phase is discharged and analyzed.

30.9 g of solution containing 1.9 g of ethyl acetate corresponding to 95% of the initially present ethyl acetate are recovered.

Example 15

44.3 g of aqueous solution containing 22.6 g of acetic acid $CH_3COOH$ are introduced into a 100 ml flask equipped with stirrer. 44.3 g of hydrofluoropolyether used in Example 1 are fed to the same. The mixture is put under stirring for 30 minutes and then discharged into a 100 ml separatory funnel.

After separation 45.2 g of a solution containing 2.02% by weight of acetic acid corresponding to 4.0% of the fed acetic acid and to the 0.01% of water are obtained.

Example 16

43.9 g of aqueous solution containing 27.5 g of methylethylketone (MEK) and 4.7 g of ethanol are introduced into a 250 ml flask equipped with stirrer. 58.7 g of hydrofluoropolyether used in Example 1 are fed to the same. The mixture is put under stirring for 30 minutes and then discharged into a 250 ml separatory funnel.

After separation 82.1 g of a solution containing 26.4% by weight of methylethylketone corresponding to 78.9% of the fed methylethylketone, 2.1% of ethanol corresponding to 36.2% of the fed ethanol and 0.8% of water are obtained.

Example 17

29.9 g of aqueous solution containing 18.6 g of methylethylketone (MEK) and 3.3 g of ethanol are introduced into a 100 ml flask equipped with stirrer. 40.7 g of hydrofluoropolyether having structure of formula (II) are fed to the same, wherein $T_1=T_2=$—$CF_2H$ and it is formed for 0.6% by weight by the oligomer having d=1 and e=0, for 20.4% by the oligomer having d=1 and e=1, for 75.9% by the oligomer having d=2 and e=0, for 2% by the oligomer having d=1 and e=2 and for 1% by the oligomer having d=2 and e=1 with number average molecular weight of 342 having a boiling point of 94.4° C., viscosity at 25° C. equal to 0.59 cSt. The mixture is put under stirring for 30 minutes and then discharged into a 100 ml separatory funnel.

After separation 60.9 g of a solution containing 28.9% by weight of methylethylketone corresponding to 94.6% of the fed methylethylketone, 3.2% of ethanol corresponding to 59% of the fed ethanol and 1.1% of water are obtained.

The invention claimed is:

1. A liquid-liquid extraction process of polar organic substances, completely or partially soluble in water, from their aqueous solutions, comprising:
   1) adding to said aqueous solutions a fluorinated extracting liquid selected from the group consisting of:
      A) hydrofluoropolyethers, and
      C) hydrofluoroethers, and
      mixtures thereof, wherein A) and C) have a molecular weight in the range 82–12,000, and when A) is a polymer the molecular weight is a number average molecular weight, with formation of an aqueous phase and of an organic phase;
   2) separating of the organic phase, formed by the fluorinated extractant containing the polar organic substance, from the aqueous phase;
   3) fractional distilling the organic phase to separate the polar organic substance from the extractant.

2. The process according to claim 1, wherein the A) hydrofluoropolyethers comprise one or more oxy(per)fluoroalkylene units selected from the group consisting of:
   —$(CF_2(CF_2)_cO)$—, wherein c=1, 2, or 3;
   —$(CF_2O)$—;
   —$(CF_2CF(CF_3)O)$—;
   —$(CF(CF_3)O)$—;
   —$(CF_2CF(OX)O)$—; and
   —$(CF(OX)O)$—, wherein X=—$(Y)_nCF_3$
      wherein Y=—$CF_2$—, —$CF_2O$—, —$CF_2CF_2O$—, or —$CF_2CF(CF_3)O$—,
      and n=0, 1, 2, 3, or 4;
   said units being statistically distributed in the polymer chain.

3. The process according to claim 1, wherein the A) hydroperfluoropolyethers have formula (I):

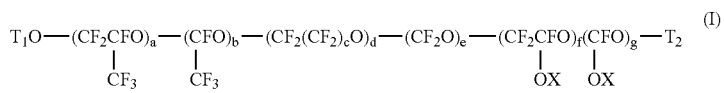

wherein X has the above meaning; the coefficients a, b, d, e, f, and g are 0 or integers, c is 1, 2 or 3, selected so that their sum results such that the number average molecular weight is in the range 82–12,000; $T_1$ and $T_2$, equal to or different from each other, are selected from the group consisting of —$CF_2H$, —$CF(CF_3)H$, —$CF_2CF_2H$, —$CH_3$, and —$C_2H_5$.

4. The process according to claim 3, wherein the number average molecular weight is in the range 180–5,000.

5. The process according to claim 1, wherein the A) hydroperfluoropolyethers have formula (II):

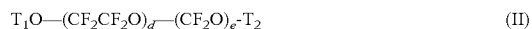

wherein $T_1$ and $T_2=$—$CF_2H$ and d and e are 0 or integers, selected so that their sum results such that the number average molecular weight is in the range 180–5,000.

6. The process according to claim 1, wherein the C) hydrofluoroethers have general formula (III):

wherein $R_1$ and $R_2$, equal to or different from each other, are alkyls comprising together at least 3 carbon atoms, wherein at least one of the $R_1$ and $R_2$ contains at least one fluorine atom and wherein the total number of the hydrogen atoms is equal at most to the number of the fluorine atoms, and optionally $R_1$ and/or $R_2$ contain one or more ether oxygen atoms.

7. The process according to claim 6, wherein, to increase the nonflammability, the number of fluorine atoms is higher than the number of hydrogen atoms.

8. The process according to claim 1, wherein the adding of the fluorinated extractant with the aqueous solution is carried out in a stirred system, at temperatures in the range 0° C.–50° C., and at atmospheric pressure or higher.

9. The process according to claim 8, wherein said temperatures are in the range 15° C.–30° C.

10. The process according to claim 1, wherein the aqueous solutions to be subjected to the extraction process contain from 0.1 to 99% by weight of completely dissolved polar organic substance.

11. The process according to claim 1, wherein the ratio by weight between the aqueous solution containing the polar organic substance and the fluorinated extractant is in the range 0.005–50.

12. The process according to claim 11, wherein the ratio by weight between the aqueous solution containing the polar organic substance and the fluorinated extractant is in the range 0.01–10.

13. The process according to claim 1, wherein A) and C) have a molecular weight in the range 180–5,000.

* * * * *